United States Patent [19]

Tamm et al.

[11] 4,204,430
[45] May 27, 1980

[54] AUTOMATIC LIQUID FLOW SAMPLING APPARATUS

[75] Inventors: Rolf Tamm, Salem; Toma Tomoff; Bernhard Huber, both of Uberlingen, all of Fed. Rep. of Germany

[73] Assignee: Bodenseewerk Perkin-Elmer & Co., GmbH, Uberlingen, Fed. Rep. of Germany

[21] Appl. No.: 874,586

[22] Filed: Feb. 2, 1978

[30] Foreign Application Priority Data

Feb. 2, 1977 [DE] Fed. Rep. of Germany ....... 2704239

[51] Int. Cl.$^2$ .............................................. G01N 1/14
[52] U.S. Cl. .................................... 73/423 A; 73/1 R
[58] Field of Search .............. 73/423 A, 1 R; 422/100

[56] References Cited

U.S. PATENT DOCUMENTS

| | | | |
|---|---|---|---|
| 3,666,420 | 5/1972 | Paatzsch | 73/423 A X |
| 4,042,338 | 8/1977 | Huber | 73/423 A X |
| 4,068,529 | 1/1978 | Konig | 73/1 R X |
| 4,080,833 | 3/1978 | Huber | 73/423 A |
| 4,111,051 | 9/1978 | Tamm et al. | 73/423 A |

Primary Examiner—Gerald Goldberg
Assistant Examiner—Joseph W. Roskos
Attorney, Agent, or Firm—S. A. Gairratana; F. L. Masselle; E. T. Grimes

[57] ABSTRACT

An automatic sampling apparatus for withdrawing samples from a continuously flowing liquid for analysis by a flameless atomic absorption spectrometer includes a sample vessel which, at predetermined times, receives pumped samples of the liquid to be tested, a neutral dilutant liquid, or a calibrated liquid for recalibrating the spectrometer system. A probe having a pipette-like tip is mechanically actuated to dip into the sample vessel and an intake and dispensing pump connected to the probe draws a small sample into the probe tip whereupon the probe mechanism lifts and rotates the probe and inserts the tip into the graphite atomizer tube of the atomic absorption spectrometer. The probe mechanism then returns the probe where it is first flushed with a flushing liquid pumped through the probe and is then returned to the sample vessel to draw the next test sample.

10 Claims, 6 Drawing Figures

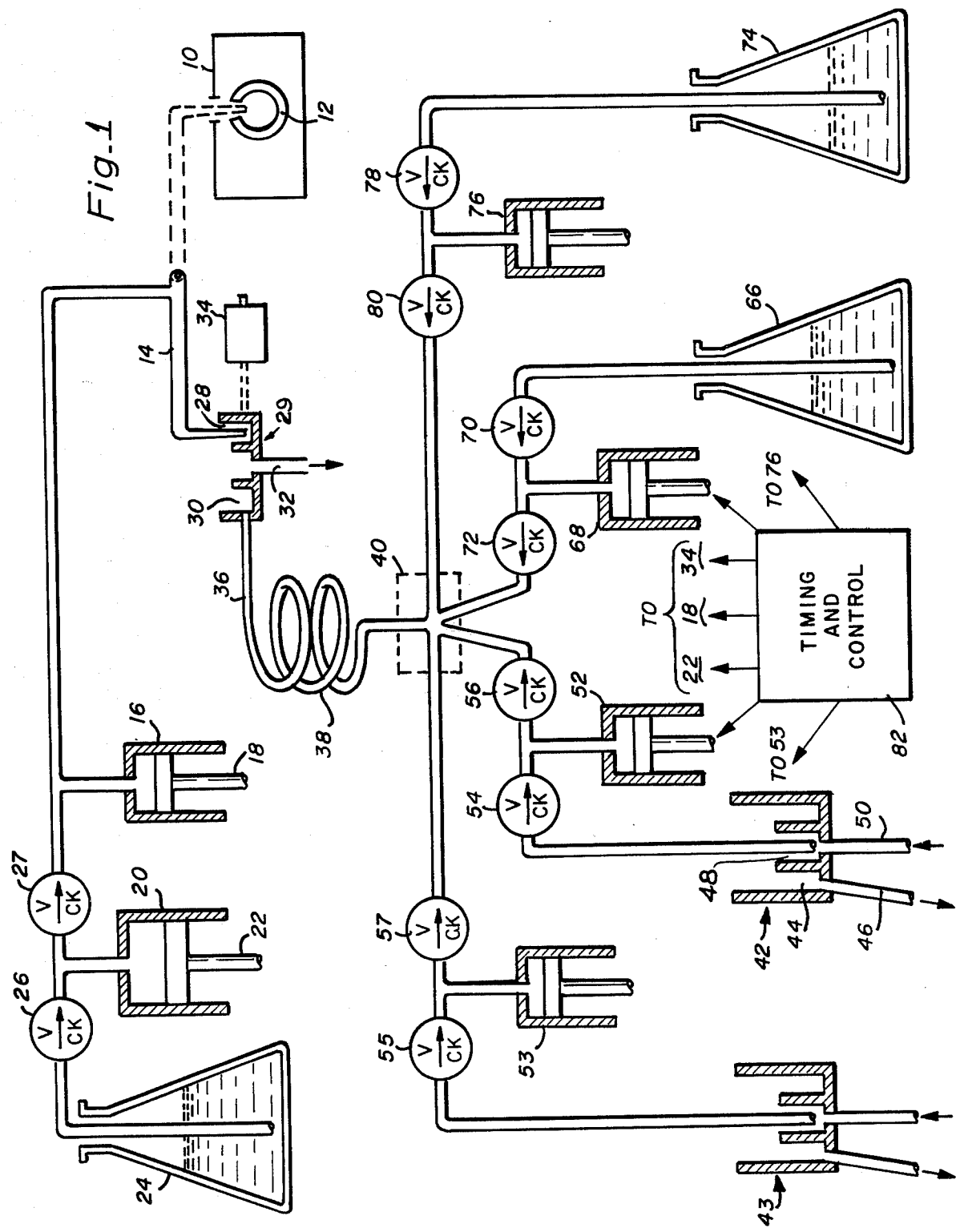

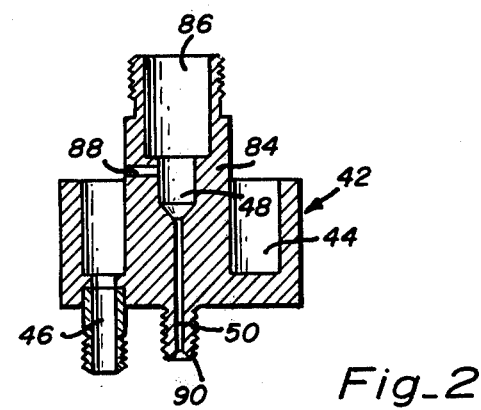
Fig_2
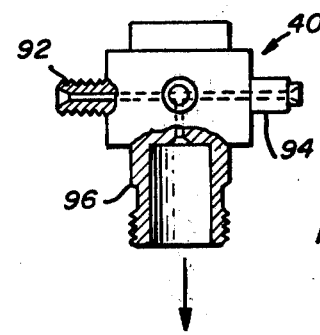
Fig_3
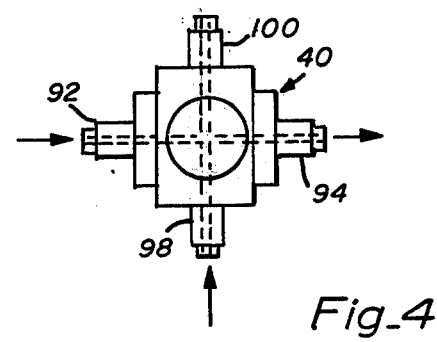
Fig_4

AUTOMATIC LIQUID FLOW SAMPLING APPARATUS

CROSS-REFERENCE TO RELATED APPLICATIONS

The automatic sampling apparatus that is the subject matter of this specification is closely related to copending application Ser. No. 688,789, filed May 21, 1976 now U.S. Pat. No. 4,111,051 issued Sept. 5, 1978, and assigned to the assignee of this present invention.

The above-referenced copending application describes and claims a liquid sampling apparatus including a turntable that carries a ring of sample containers to a station where a probe hagving a pipette-like tip withdraws a sample of the liquid and thereupon is automatically rotated by an associated mechanism to discharge the sample into the intake port of a graphite atomizer tube of an atomic absorption spectrometer. The probe mechanism then returns the probe tip to a rinse vessel so that a pump associated with the probe can draw and then discharge a cleansing fluid that will prevent pre-contamination of the probe tip prior to its being inserted into the next sample container.

Prior to the invention described in the above-referenced copending application, liquid samples of material were normally introduced manually into the sample port of the heated graphite tube of the atomic absorption spectrometer by means of a syringe or micropipette. The sample was atomized by the heated graphite furnace and the spectral beam passing longitudinally through the graphite tube provided the desired spectroscopic analysis. The turntable sampling system and the automatically positioned pipette described in the copending application thus provided great advantages over the prior art. While the invention described in the copending application is quite adequate for normal laboratory analyses, it requires the manual steps of rinsing and re-loading each sample chamber and placing it on the turntable and is therefore not suitable for completely automated analytical operations.

The present invention is completely automatic and may be carried out without need of an attending technician.

BRIEF SUMMARY OF THE INVENTION

Briefly described, the invention includes the prior art probe and its associated drive mechanism for inserting the pipette-like probe tip into a small sample vessel and then lifting and rotating the probe to insert the tip into the sample port of a graphite atomizer tube of an atomic absorption spectrometer. Connected to the probe is an intake and dispensing pump that enables the probe to draw and discharge fluids through its tip, and also a flushing pump that forces a flushing liquid through the probe to clean the bore of the tip. A sample cup is positioned to supply a liquid sample to the probe tip and is movable by a suitable positioning mechanism so that the probe tip may first dip into a flushing cup into which the flushing liquid is discharged from the tip to cleanse the exterior of the tip and then dip into the sample cup to draw a sample of liquid for analysis. A Central control system which controls the operation of the flushing pump, the intake and dispensing pump, the probing drive means, and the sample and flushing vessel positioning mechanism is also programmed to control pumps that inject into the sample cup either samples of the liquid to be analyzed, a dilutant or blank testing sample that is used to "thin" the liquid to an appropriate concentration for proper atomizing, or a calibration liquid of known composition for the purpose of calibrating the analytical system. The sample liquid to be tested is continually flowing through a sampling fixture that may divert a small amount of liquid from a large pipe, such as a waste or sewer main and, when actuated by the control system, a small sample is pumped from the sample fixture through a duct in the bottom of the sample cup along with the predetermined quantity of the dilutant, if necessary. The injected sample liquid purges the sample cup of the previous sample which overflows the vessel into a drain system.

DESCRIPTION OF THE DRAWINGS

In the drawings which illustrate a preferred embodiment of the invention:

FIG. 1 is a simplified schematic diagram of the apparatus of the invention;

FIG. 2 is a sectional elevation view illustrating the fluid sampling fixture from which samples of the test fluid are pumped;

FIG. 3 is a sectional elevation view illustrating a preferred embodiment of the conduit junction through which all test samples, dilutant, and calibration samples are transmitted to the sample vessel;

FIG. 4 is a plan view of the conduit junction illustrated in FIG. 3;

DETAILED DESCRIPTION OF THE PREFERRED EMBODIMENT

Figure 5:
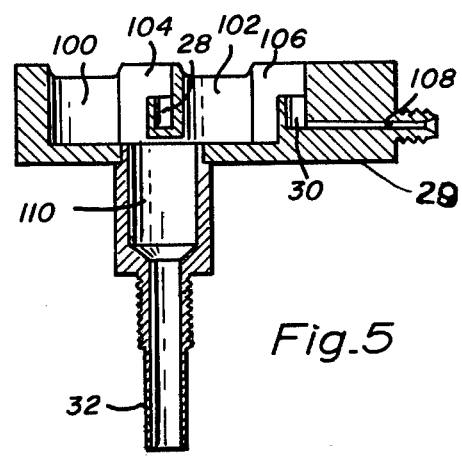
FIG. 5 is a sectional elevation view of the vessel containing the sample and flushing cups.

In the system schematic diagram of FIG. 1, the reference numeral 10 represents an atomic absorption spectrometer having a graphite tube atomizer 12 into which a sample, in liquid form, is inserted and rendered into an atomic state by heating of the graphite tube 12. As originally conceived, the atomization was carried out by spraying a nebulized vapor of the liquid sample into an open flame. More recently, however, there has been an increasing use of flameless atomization which has certain technical advantages particularly for certain elements. The most common form of flameless atomizers is a heated graphite furnace, such as the atomizer tube 12, which typically is electrically heated by passing a current between the electrode disposed at the respective ends of the tube. The sample is then introduced through a radial port in the wall of the tube and the spectroscopic analysis is carried out by passing the spectral beam longitudinally through the tube 12.

In the system illustrated in FIG. 1, liquid samples are introduced into a radial port in the graphite tube atomizer 12 by an intake and dispensing tube 14 having a pipette-like tip and an associated mechanism (not shown) for lifting the tube 14 and rotating it about its longitudinal axis so that, at both limits of movement about the transverse axis, the probe tip is directed generally downward into either the radial port of the graphite tube atomizer 12, as illustrated by the dashed lines of the tube 14, or into a compartmented vessel when swung to its opposite limit of displacement, as will be subsequently described in detail. The intake and dispensing tube 14 and the mechanism employed to lift and swing the tube tip between the compartmented vessel and the graphite tube atomizer is prior art and is described in detail in the aforementioned copending patent application Ser. No. 688,789. It is, therefore, unnecessary to describe in detail the mechanism in this specification.

Coupled to the bore of the intake and dispensing tube 14 is an intake and dispensing pump 16 which may be a typical piston pump having a suitable means for driving the shaft 18. Pump 16 preferably has a small bore and stroke since it normally is required to draw or discharge only approximately 20 microliters of fluid through the tip of the tube 15.

Coupled into the conduit between the pump 16 and the tube 14 is a flushing pump 20 provided with a suitable drive means for actuating the piston rod 22. Flushing pump 20 is coupled to a flushing liquid container 24 and is provided with check valves 26 and 27 so that approximately 1 milliliter of flushing liquid will be drawn by the pump 20 through the valve 26 and will be discharged through valve 27 and through the intake and dispensing tube 14.

As illustrated in FIG. 1, the intake and dispensing tube 14 is positioned so that its pipette-like tip is in the flushing cup 28 of a compartmented vessel 29 which also includes a sample cup 30 and a drain 32. Both the cups 28 and 30 are overflow types of cups which will overflow into a common drain 32, as will be later described in detail in connection with FIG. 5. The compartmented vessel 29 is movable laterally by an electrical power source 34 which may be a geared electrical motor with a pinion gear that drives a rack connected to the compartmented vessel 29.

The operation of the system to this point is as follows: A liquid may be either a calibration sample, or a fluid sample with or without a dilutant, is pumped into the bottom of a sample cup 30 through a conduit 36. During the filling of the sample cup 30, drive means 22 associated with the flushing pump 20 is activated to force approximately 1 milliliter of flushing liquid from the container 24 through the dispensing tube 14 and into the flushing cup 28. The intake and dispensing tube 14 is then raised by its associated mechanism (not shown) and the drive means 34 is activated to position the sample cup 30 of the compartmented vessel 29 under the pipette-like tip of the tube 14. As the intake and dispensing tube 14 is lowered into the sample cup 30, the drive means associated with the intake and dispensing pump 16 is activated and a small slug of air followed by approximately 10 microliters of the sample in cup 30 is drawn into the tube 14, the air slug providing effective isolation of the flushing liquid from the fluid sample. The associated mechanism then lifts and rotates the tube 14 and inserts the pipette-like tip into the port of the graphite tube atomizer 12 of spectrometer 10. The pump drive means associated with the pump 16 then discharges into the graphite tube 12 a portion of the sample contained in the tube 14. Drive means 34 then returns the compartmented vessel 29 so that when the dispensing tube 14 is repositioned, it enters the flushing cup 28, at which time the flushing pump 20 forces the flushing liquid through the tube 14 to purge the remainder of the sample remaining in the tube 14 as well as substantially fill the flushing cup 28 with clean uncontaminated flushing liquid.

Liquid samples to be tested are admitted into the system by way of the sampling fixture 42 or additional sample fixtures, such as the fixture 43, which is identical to the fixture 42. The sampling fixture 42 includes an inlet duct 50 through which the sample fluid is admitted into a central bore 48 which overflows into an overflow cup 44 and out through an outlet duct 46, as shown in FIG. 1. In the detailed diagram of the fixture in FIG. 2, it can be seen that the inlet duct 50 is a small diameter and the overflow from the bore 48 is carried by a larger diameter duct 88 interconnecting the bore 48 with the overflow cup 44. Liquid to be sampled enters a small conduit terminating within the bore 48 and is pumped by a pump 52 through check valves 54 and 56 to a conduit junction 40, as shown in FIG. 1. Similarly, liquid samples entering the inlet duct of the second sample fixture 43 are pumped by the pump 53 through check valves 55 and 57 to the conduit junction 40. In a similar manner, calibration samples contained in the flask 66 are pumped by the pump 68 through check valves 70 and 72 to the conduit junction 40 and a dilutant or blank test sample contained in the flask 74 may be pumped by the pump 76 through check valves 78 and 80 to the conduit junction 40.

The operation of all pumps 52, 53, 20, 16, 68 and 76, together with the operation of the drive means 34 and the mechanism for lifting and rotating the intake and dispensing tube 14 is controlled by a timing and control system 82. The control system 82 also provides control signals to the atomic absorption spectrometer 10 upon actuation of the calibration sample pump 68 or the dilutant pump 76 so that the spectrometer control circuit may effect an automatic zero adjustment (auto-null) or an automatic calibration (auto concentration) function. A selector switch associated with the timing and control system 82 may be manually set to control the frequency at which calibration is to be made. Furthermore, the timing control system 82 must determine the period of operation of each of the drive means associated with each of their respective pumps and must properly time the pumping of a dilutant to provide the proper concentration in the sample cup 30. It will be appreciated that the timing and control circuit 82 cannot precisely synchronize the beginning and end of the piston movements of the various pumps and it may be necessary to provide an extra length of conduit, such as the delay conduit 38, between the conduit junction 40 and the sample cup 30 to assure that the sample fluid is properly concentrated with the dilutant at the time it reaches the sample cup and that the sample fluid does not enter the sample cup prior to the sampling by the intake tube 14.

FIG. 2 is a sectional elevation view of the sampling fixture, such as fixtures 42 or 43. The fixtures are connected to pipes carrying a flow of the fluid to be sampled so that a small portion of the fluid continually flows through the narrow inlet duct 50 into the bore 48 where it overflows through a duct 88 into the overflow cup 44 and out through the drain 46. A sample of the fluid is therefore always present in bore 48 or counterbore 86 of the fixture and is withdrawn through a tube terminating within the bore 48.

FIGS. 3 and 4 are elevation and plan views, respectively, of the conduit junction 40 into which the sample fluids, calibration sample and the dilutant or test blank sample flow prior to passing through the conduit 36 into the bottom of sampling cup 30. In the preferred embodiment, a conduit from the bore of the sampling fixture 43 is connected to the inlet terminal 92 of the conduit junction 40 and the conduit from the sampling fixture 42 is connected to the inlet terminal 98. The dilutant solution from the flask 74 is admitted into the intake connector 100 and the calibration sample from the flask 66 is admitted into the inlet terminal 96. As shown in FIG. 3, inlet connector 96 has a large bore which is provided to contain the check valve 72.

Figure 6:
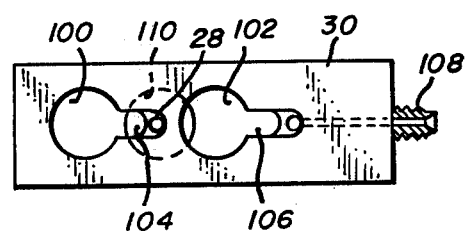
FIG. 6 is a plan view of the vessel illustrated in FIG. 5.

FIGS. 5 and 6 are a sectional elevation view and a plan view of the compartmented vessel 29 showing the small flushing cup 28 and the sample cup 30 which is filled at its bottom through an inlet duct 108. As previously mentioned, cups 28 and 30 are overflow cups which spill their contents into the recesses 104 and 106, respectively, and the cavities 100 and 102, respectively, both of which drain into the common drain 110. Each of cups 28 and 30 have a small capacity, for example, in the order of one-half milliliter, and are readily flushed by either the admission of a new fluid through the inlet duct 28 or by the flushing liquid aspirated through the intake and dispensing tube 14.

What is claimed is:

1. Apparatus for the continuous and automatic sampling and conveying of fluids to an analytical instrument, said apparatus including:
   a movable vessel having therein a flushing cup and a sample fluid cup;
   an intake and dispensing tube having an apertured tip movable between a first position in said flushing cup and a second position in the sample input port of the analytical instrument;
   first means for moving said vessel whereby the positions of said sample fluid cup and said flushing cup are exchanged;
   second means for moving said intake and dispensing tube tip between said first and second positions;
   a first pump coupled to said intake and dispensing tube for drawing and discharging a fluid through said tube;
   a second pump coupled to said intake and dispensing tube and to a source of flushing fluid for discharging said flushing fluid through said tube;
   a third pump coupled to a fluid sampling fixture and to a conduit entering the bottom of said sample fluid cup of said movable vessel for admitting a sample of fluid to said sample fluid cup; and
   timing and control means coupled to said first means, said second means, said first pump, said second pump and said third pump for sequentially pumping fluid into said sample fluid cup, drawing a sample into said intake and dispensing tube, moving said tube from its first position to its second position, aspirating said tube, moving said movable vessel, returning said tube tip to said flushing vessel, pumping flushing fluid through said tube, lifting said tube, moving said vessel, and lowering said tube tip into said sample fluid cup,
   a fourth pump coupled to said sample fluid cup and to a source of a calibration fluid, said timing and control means controlling the operation of said fourth pump to introduce said calibration fluid into said sample fluid cup at predetermined intervals for calibration of said analytical instrument,
   a fifth pump coupled to said sample fluid cup and to a source of a sample fluid dilutant, said timing and control means controlling the operation of said fifth pump to introduce said dilutant in a predetermined quantities simultaneously with samples of fluid to be analyzed,
   said sample fluid cup constituting an overflow cup which, when flooded, drains into a drain cavity through said movable vessel,
   said sample fluid fixture comprising a vessel having a tubular bore having a concentric inlet duct for admitting a sample liquid into said bore, said vessel having an overflow cup concentric with said bore and separated therefrom by a wall, said wall having a duct interconnecting said bore and said overflow cup, said bore having a larger diameter than the bore of said inlet duct, said overflow cup having an outlet drain.

2. The apparatus claimed in claim 1 further including a sixth pump interconnecting said sample fluid cup with a second source of a second sample fluid, said sixth pump controlled by said timing and control means.

3. The apparatus claimed in claim 2 further including a conduit junction interconnecting said sample fluid cup with said third, fourth, fifth and sixth pumps, said junction having four ports and four interconnecting passages lying in one plane and a fifth port having a passage interconnecting said four passages at right angles to said four passages.

4. The apparatus claimed in claim 3 further including a delay conduit interposed between said conduit junction and said sample fluid cup for controlling the transmission time of fluids between said conduit junction and said sample cup.

5. Apparatus for the continuous and automatic sampling and conveying of fluids to an analytical instrument, said apparatus including:
   a movable vessel having therein a flushing cup and a sample fluid cup;
   first means for moving said vessel between positions with the location of the sample fluid cup and said flushing cup interchanged;
   an intake and dispensing tube having an apertured tip movable between a first position in either said sample fluid cup or said flushing cup in accordance with the position of said movable vessel and a second position in the sample input port of the analytical instrument;
   a second means for moving said intake and dispensing tube tip between said first and second positions;
   a first pump coupled to said intake and dispensing tube for drawing and discharging a fluid through said tube;
   a second pump coupled to said intake and dispensing tube and to a source of flushing fluid for discharging said flushing fluid through said tube;
   a fluid sampling fixture;
   a third pump coupled to said fluid sampling fixture and to a conduit in communication with said sample fluid cup of said movable vessel for admitting a sample of fluid from said fluid sampling fixure to said sample fluid cup; and
   timing and control means coupled to said first means, said second means, said first pump, said second pump and said third pump for sequentially pumping sample fluid into said sample fluid cup, drawing a sample into said intake and dispensing tube, moving said tube from its first position to its second position, aspirating said tube, moving said movable vessel, returning said tube tip to said flushing vessel, pumping flushing fluid through said tube, lifting said tube, moving said vessel, and lowering said tube tip into said sample fluid cup.

6. The apparatus according to claim 5 including a conduit for supplying fluid substantially continuously to said sample fluid cup, said sample fluid cup constituting an overflow cup, a drain conduit coupled to said sample fluid cup for draining overflow therefrom.

7. The apparatus according to claim 6 further including a fourth pump coupled to said sample fluid cup through said supply conduit and to a source of a calibration fluid, and wherein said timing and control means controls the operation of said fourth pump to introduce said calibration fluid into said sample fluid cup through said supply conduit at predetermined intervals for calibration of said analytical instrument.

8. The apparatus according to claim 7 further including a fifth pump coupled to said sample fluid cup through said supply conduit and to a source of a sample fluid dilutant, and wherein said timing and control means controls the operation of said fifth pump to introduce said dilutant through said supply conduit in predetermined quantities simultaneously with samples of fluid to be analyzed.

9. The apparatus according to claim 5 including a sixth pump interconnecting through said supply conduit said sample fluid cup with a second source of a second sample fluid, said sixth pump controlled by said timing and controlled means.

10. The apparatus according to claim 5 including means for substantially continuously supplying sample fluid to said sample fluid fixture, said fixture constituting an overflow fixture and having a drain conduit for draining overflow therefrom.

* * * * *